(12) United States Patent
Doll

(10) Patent No.: US 12,272,513 B2
(45) Date of Patent: Apr. 8, 2025

(54) ELECTRON EMITTER STRUCTURE, EXTERNAL PHOTOELECTRIC EFFECT EMITTER, PARTICLE COLLECTING DEVICE, TUNNEL SURFACE EMITTER, SEMICONDUCTOR- BASED DIRECT EMITTER AND LIQUID IONISER COMPRISING SAME, GAS SENSOR COMPRISING AN EMITTER OR EMITTER STRUCTURE, METHOD FOR GENERATING FREE ELECTRONS, AND METHOD FOR COLLECTING PARTICLES

(71) Applicant: DBT GMBH, Wuerzburg (DE)

(72) Inventor: Theodor Doll, Isernhagen (DE)

(73) Assignee: DBT GMBH, Wuerzburg (DE)

( * ) Notice: Subject to any disclaimer, the term of this patent is extended or adjusted under 35 U.S.C. 154(b) by 0 days.

(21) Appl. No.: 17/926,139

(22) PCT Filed: May 17, 2021

(86) PCT No.: PCT/DE2021/100436
§ 371 (c)(1),
(2) Date: Mar. 21, 2023

(87) PCT Pub. No.: WO2021/233501
PCT Pub. Date: Nov. 25, 2021

(65) Prior Publication Data
US 2024/0266134 A1      Aug. 8, 2024

(30) Foreign Application Priority Data
May 18, 2020   (DE) .................... 10 2020 113 351.0

(51) Int. Cl.
*H01J 1/34*      (2006.01)
*G01N 27/64*   (2006.01)
*H01J 3/02*      (2006.01)

(52) U.S. Cl.
CPC ................ *H01J 1/34* (2013.01); *G01N 27/64* (2013.01); *H01J 3/021* (2013.01); *H01J 2201/3425* (2013.01)

(58) Field of Classification Search
USPC ................................................... 324/464, 316
See application file for complete search history.

(56) References Cited

U.S. PATENT DOCUMENTS 4,370,797 A    2/1983   van Gorkom et al.
5,154,733 A    10/1992  Fujii et al.
(Continued)

FOREIGN PATENT DOCUMENTS

DE               690 09 357 T2     10/1994
DE       10 2011 013 262 A1        9/2012
(Continued)

OTHER PUBLICATIONS

P. Begley et al.: "Photoemissive ionisation source for ion mobility detectors", Journal of Chromatography, vol. 588, pp. 239-249 (1991).

(Continued)

*Primary Examiner* — Vincent Q Nguyen
(74) *Attorney, Agent, or Firm* — Norman B. Thot

(57) ABSTRACT

An electron emitter structure includes an electron emission layer which is arranged to have a first side and a second side, and an electron accelerating structure which is arranged on the first side of the electron emission layer. The electron emission layer has a mixture of metals so as to be atmospherically stable. The electron accelerating structure has at least one electrode which is electrically insulated from the electron accelerating structure so as to form an acceleration path which allows electrons which are released from the electron emission layer to be selectively accelerated upon (Continued)

generation of an adjustable electric field. The acceleration path has a length l of from 10 nm to 1 μm.

20 Claims, 5 Drawing Sheets

(56) References Cited

U.S. PATENT DOCUMENTS

| | | | | |
|---|---|---|---|---|
| 5,729,094 | A * | 3/1998 | Geis | H01J 1/304 |
| | | | | 313/496 |
| 6,023,124 | A * | 2/2000 | Chuman | H01J 1/312 |
| | | | | 257/11 |
| 6,538,256 | B1 | 3/2003 | Mankos et al. | |
| 6,794,805 | B1 | 9/2004 | Hatai et al. | |
| 2003/0010996 | A1 | 1/2003 | Hongo | |
| 2003/0102793 | A1 | 6/2003 | Komoda et al. | |
| 2004/0135518 | A1 | 7/2004 | Brune et al. | |
| 2006/0090996 | A1 | 5/2006 | Yaniv et al. | |
| 2006/0290291 | A1 | 12/2006 | Aizawa | |
| 2017/0023524 | A1 | 1/2017 | Boumsellek | |

FOREIGN PATENT DOCUMENTS

| | | |
|---|---|---|
| EP | 0 416 626 A2 | 3/1991 |
| EP | 0 445 787 A1 | 9/1991 |
| EP | 1 026 721 A1 | 8/2000 |
| EP | 1 320 116 A1 | 6/2003 |
| EP | 3 121 835 A1 | 1/2017 |
| JP | S47-25193 B | 7/1972 |
| JP | S51-9586 A | 1/1976 |
| JP | S63-150837 A | 6/1988 |
| JP | H03-29259 A | 2/1991 |
| JP | H04-152296 A | 5/1992 |
| JP | H04-171062 A | 6/1992 |
| JP | H05-4055 A | 1/1993 |
| JP | 2003-031112 A | 1/2003 |
| JP | 2017-27939 A | 2/2017 |
| JP | 2018-41736 A | 3/2018 |
| WO | WO 01/26134 A1 | 4/2001 |
| WO | WO 02/05305 A1 | 1/2002 |
| WO | WO 02/15223 A1 | 2/2002 |
| WO | WO 2005/052978 A2 | 6/2005 |
| WO | WO 2009/066723 A1 | 5/2009 |

OTHER PUBLICATIONS

H-I. Jung et al.: "Low-voltage and low-power field-ionization gas sensor based on micro-gap between suspended silver nanowires electrodes for toluene detection", MEMS Conference on Micro Electro Mechanical Systems, pp. 195-198 (2017).

* cited by examiner

ELECTRON EMITTER STRUCTURE, EXTERNAL PHOTOELECTRIC EFFECT EMITTER, PARTICLE COLLECTING DEVICE, TUNNEL SURFACE EMITTER, SEMICONDUCTOR- BASED DIRECT EMITTER AND LIQUID IONISER COMPRISING SAME, GAS SENSOR COMPRISING AN EMITTER OR EMITTER STRUCTURE, METHOD FOR GENERATING FREE ELECTRONS, AND METHOD FOR COLLECTING PARTICLES

CROSS REFERENCE TO PRIOR APPLICATIONS

This application is a U.S. National Phase application under 35 U.S.C. § 371 of International Application No. PCT/DE2021/100436, filed on May 17, 2021 and which claims benefit to German Patent Application No. 10 2020 113 351.0, filed on May 18, 2020. The International Application was published in German on Nov. 25, 2021 as WO 2021/233501 A1 under PCT Article 21(2).

FIELD

The present invention relates to an electron emitter structure, in particular for emitting electrons of defined low energy under atmospheric conditions, and to an external photoelectric effect emitter, a particle collection device, a tunnel surface emitter, a semiconductor-based direct emitter comprising the same, a liquid ionizer comprising the same, a gas sensor comprising an emitter or an emitter structure, a method for generating free electrons via the same, and a method for collecting particles via the same.

BACKGROUND

Low energy electrons are used, for example, for air purification or trace gas analysis. Charges are needed to form ions in the air. These charges are created by irradiating the air molecules with high energy electromagnetic radiation, by radioactive sources, or by electron sources. The charges form bonds with the air molecules. When charges are generated by high energy electromagnetic radiation and by radioactive sources, a variety of ion types are formed due to high and fuzzy energies during charge generation or also by charge transfer. Electrons are released into the air molecules for the formation of ions in air via electron sources. Low energy electrons can ionize these molecules. The ions formed in this way can be captured in an electric field and thus removed from the ambient air. Dust particles, harmful substances, contaminants, as well as mites, pollen, odors, germs and bacteria can, for example, thereby be bound. Such electron sources can therefore be used in air purifiers. Whether the electrons can be captured by the molecules depends substantially on the energy of the electrons. Different molecules can capture electrons of different energies. Only certain molecules can be charged by electrons with a very sharp energy distribution in a low energy range. Such electrons are thus also suitable for the ionization of molecules for trace gas analysis, for example, by mass spectrometry.

Ion formation with UV sources in photoionization detectors (PID sensors), ionization with 63Ni sources in analytical devices, or electron impact ionization in vacuum in mass spectrometers have previously been described. UV sources are also used for ionization in air purifiers. This also produces ozone, which also contributes in part to air purification. However, the decomposition products of nicotine and cigarette smoke with the ozone, in addition to the ozone itself, pose high health risks. Ozone generating air purifiers are therefore disadvantageous.

UV sources in PID sensors ionize via the Compton effect all molecules of which the ionization energy E is below the photon energy hv. This produces a broad spectrum of molecules ionized to different extents that is less suitable for precision applications such as the trace gas analysis mentioned above.

Free electrons in air can be generated by field emission or thermal emission. In the case of field emission, electrons are released from a negatively charged electrode by a strong electric field using the tunnel effect. Thermal emission refers to the thermally induced flow of electrons from a surface or across a potential barrier. In this process, the electrons in the carrier overcome the work function of the material by thermal energy supplied to them. Thermal emission is more difficult to generate under atmospheric conditions than field emission, but could be generated with high temperature, oxidation stable materials such as $SnO_2$ or antimony doped $SnO_2$.

Electrons can also be generated by the external photoelectric effect. An electron is here released from a bond in a solid by absorbing a photon. In the prior art, a so called electron ionization detector ("ePID") is known which generates electrons of very low energy from an emitter material on the basis of the external photoelectric effect and accelerates them to path lengths of the order of a few mean free path lengths of the molecules under normal conditions in an electric field. The electron energy is thereby theoretically freely adjustable, whereby different trace gases in air can be identified not only in terms of total quantity but also on the basis of their ionization energies to a certain extent. UV light emitting sources such as diodes (UV LEDs) are used to release electrons.

Emissive materials with a low work function are in principle best suited to generate free electrons in air. These materials have a high density of emitting electrons, i.e., they have a high electron density at the Fermi level or at the valence band edge. The materials having a low work function of about 1 2 eV used thus far for this purpose, such as Ba, BaO, Cs, i.e., alkali and alkaline earth metals and their semiconducting oxides, are, however, highly reactive in air, i.e., they oxidize exothermically or form a hydroxide. They can therefore only be used under high vacuum conditions. Lanthanum boride, which is used, for example, for electron emission in field emitter tips of electron microscopes, is also unsuitable for applications under atmospheric conditions since, before being used as an electron emitter, it must be freed from its surface oxide at high temperatures in a vacuum. An application in air leads to re oxidation and would therefore not be possible, or would only be possible for a very short time (for example, for a few µs).

Precious metals, such as gold, platinum and silver, are stable to oxidation or form only the thinnest oxide or sulfide layers, which can easily be tunneled through, but have very high work functions in the range of 4.8 to 5.6 eV. This energy range is still not accessible for UV LEDs. The situation is similar with metals that occur "native", i.e., as pure metals with only light oxidic coatings. Arsenic, antimony, tellurium, lead, bismuth, indium and tin belong to this group. They usually have work functions of more than 4 eV and their oxides have comparable values. The subgroup metals, especially valve metals, of which the work functions are about 1 eV lower than those of the native metals, usually form insulating, electron poor oxides with thicknesses that are above the usual tunnelling distance of 5 nm. The work functions of their oxides is usually not significantly lower than that of the pure metals, although some have at least conduction electrons as semiconductors (NiO, $CuO_x$, $CoO_x$, $Cr_2O_3$, $SnO_2$).

Lanthanum and similar rare earth metals of the same group, because of their proximity to the alkaline earth metals, have a lower and thus more suitable work function range from 2.5 to 3.6 eV as do their oxides. These materials are not, however, stable when exposed to atmospheric humidity (they form hydroxides and oxidize completely over their entire volume).

An exception with unique properties is thorium with a work function of 2.2 2.4 eV, a work function of the oxide of 2.8 eV, and stability towards the air components. Because of its radioactivity, but especially because of the high energy of the emitted alpha particles of 54 MeV, which ionize non-specifically, this material is not suitable for applications requiring a low, sharp electron energy. Cerium, samarium and ytterbium (and the normal subgroup elements yttrium and strontium) are used as thorium substitutes in other applications. As pure metals, however, they are subject to the limitations of lanthanides in that they oxidize quickly and react with water, and are therefore also out of the question.

The ePID designs known from the prior art can therefore not be operated under atmospheric conditions with long term stability. This makes it impossible to use them in electrostatically operated air purifiers that work without ozone. Analytical methods such as mass spectroscopy are also not possible under atmospheric conditions with the ePID designs known from the prior art. Free electrons in the air that have the most precise (sharpest) energies possible in the range of, for example <25 eV, are required therefor. Also missing is a highly emissive material that is atmospherically stable, i.e., stable in the long term, against oxygen and humidity and that has the lowest possible work function. Such a material would allow the use of low cost light sources (e.g., UV LED) for the external photoelectric effect.

SUMMARY

An aspect of the present invention is to provide an efficient emitter for low energy electrons in the range of less than 25 eV with a narrow energy width which can be operated with long term stability.

In an embodiment, the present invention provides an electron emitter structure which includes an electron emission layer which is arranged to have a first side and a second side, and an electron accelerating structure which is arranged on the first side of the electron emission layer. The electron emission layer comprises a mixture of metals so as to be atmospherically stable. The electron accelerating structure comprises at least one electrode which is electrically insulated from the electron accelerating structure so as to form an acceleration path which is configured to allow electrons which are released from the electron emission layer to be selectively accelerated upon generation of an adjustable electric field. The acceleration path has a length l of from 10 nm to 1 μm.

BRIEF DESCRIPTION OF THE DRAWINGS

The present invention is described in greater detail below on the basis of embodiments and of the drawings in which.

DETAILED DESCRIPTION

Figure 1:
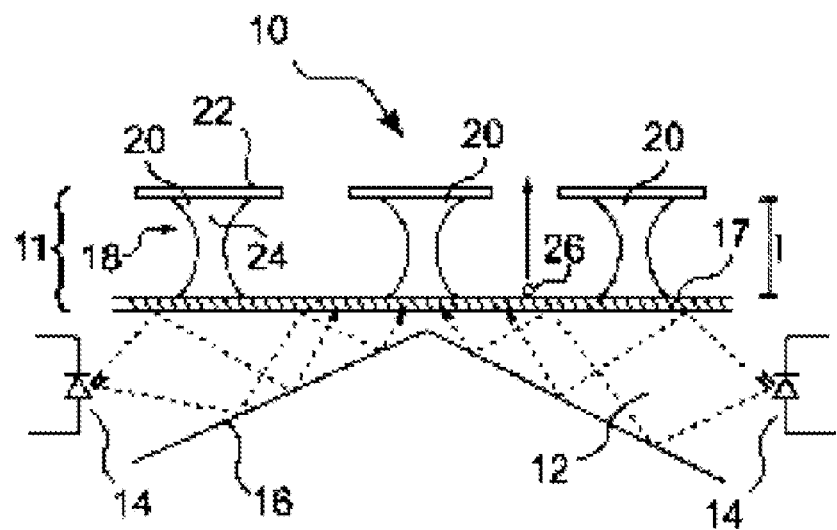
FIG. 1 shows a sectional view of an external photoelectric effect emitter according to an embodiment of the present invention.

The present invention provides an electron emitter structure comprising: a) an atmosphere stable electron emission layer of a mixture of metals, wherein the atmosphere stable electron emission layer has a first side and a second side; and b) an electron accelerating structure on the first side of the electron emission layer having at least one electrode electrically insulated from the electron accelerating structure to form an acceleration path configured to allow electrons released from the electron emission layer to be selectively accelerated upon generation of an adjustable electric field, and wherein the acceleration path has a length l in a range from 10 nm to 1 μm.

Only mixtures of elementary metals, i.e., metals in the oxidation state 0, are to be understood as metals in the mixture of metals. Metal oxides are in particular thus not understood as metals according to the present invention.

The mixture of metals is advantageously an alloy, for example, comprising a compound selected from InCe, AsCeSm, AgSm, AgCe, AgSmCe and AgAsCeSm and/or two or more elements from As, Ag, Zn, Au, Pt, Ru Rh, Pd, Os, Ir, Ce, Zn, Bi, Te, Sm, Eu, Gd, Yt, Yb, Nd, Pr and La.

The mixture of metals alternatively or additionally comprises a eutectic comprising at least one noble metal, at least one lanthanide, and at least one element selected from As, Te, Bi and Sn.

With regard to the mixture of metals, "comprise" can, for example, mean "consist of".

Eutectics are understood to mean combinations of materials at their eutectic points or in the vicinity of the eutectic points.

The electron accelerating structure advantageously further comprises at least one insulating structural element which, together with the at least one electrode, forms at least one electron accelerating element.

An embodiment of the present invention provides that the at least one insulating structural element is arranged between and connected to the electron emission layer and the at least one electrode.

In an embodiment of the present invention, the electron emitter structure comprises a plurality of electron accelerating elements arranged in an array, for example, laterally.

The present invention further provides an external photoelectric effect emitter comprising an electron emitter structure according to any of the aforementioned embodiments, and one or more UV LEDs for releasing electrons from the electron emission layer, wherein the one or more UV LEDs is or are configured to emit electromagnetic radiation at least partially onto the electron emission layer.

In an embodiment of the present invention, the external photoelectric effect emitter further comprises a substrate arranged on the second side of the electron emission layer, wherein the one or more UV LEDs is or are configured to emit electromagnetic radiation at least partially onto the second side of the electron emission layer and is or are arranged outside and/or inside the substrate, and the substrate is at least partially transparent in the emission wavelength range of the UV LEDs.

The external photoelectric effect emitter advantageously further comprises a reflective layer arranged on a side of the substrate facing away from the electron emission layer.

In the external photoelectric effect emitter, the reflective layer expediently comprises a material selected from platinum, mercury, nickel, palladium and iridium.

In an embodiment of the present invention, the one or more UV LEDs in the external photoelectric effect emitter are configured to emit electromagnetic radiation at least partially onto the first side of the electron emission layer.

It can in particular be provided that the electron accelerating structure is at least partially transparent in the emission wavelength range of the UV LEDs.

The present invention also relates to a particle collection device comprising an external photoelectric effect emitter, and two plates electrically chargeable with different polarity for generating an electric field, which are arranged on the first side of the electron emission layer at a distance from each other and in each case perpendicular to the electron emission layer.

The present invention further provides a tunnel surface emitter comprising an electron emitter structure, an insulator layer arranged on the second side of the electron emission layer and having a layer thickness between 0.5 nm and 6 nm, and a metal layer arranged on the insulator layer on a side facing away from the electron emission layer and having a layer thickness between 0.5 nm and 6 nm, wherein both the electron emission layer and the insulator layer have layer thicknesses that can be tunneled through. Layer thicknesses that can be tunneled through can, for example, be in the range between 0.5 nm and 5 nm.

The present invention further provides a semiconductor based direct emitter for use in surface chemistry comprising an electron emitter structure, an insulator layer arranged on the second side of the electron emission layer and having a layer thickness that can be tunneled through, and a semiconductor arranged on a side of the insulator layer facing away from the electron emission layer, the semiconductor having n doped regions and p doped regions arranged in alternation next to one another, wherein the n doped regions and the p doped regions have boundary regions adjacent to the insulator layer.

The semiconductor based direct emitter advantageously further comprises an insulator arranged on a side of the semiconductor facing away from the insulator layer, wherein the insulator has fingers arranged at boundary regions between the n doped regions and the p doped regions and projecting into the semiconductor.

The present invention further relates to a semiconductor based direct emitter comprising an electron emitter structure, an insulator layer arranged on the second side of the electron emission layer and having a layer thickness that can be tunneled through, and a light emitting device, selected from a VCSEL, a side emitting semiconductor laser or a light emitting diode, arranged on a side of the insulator layer facing away from the electron emission layer.

The present invention further provides a liquid ionizer comprising a semiconductor based direct emitter, and a protective layer arranged on a side of the electron accelerating structure facing away from the electron emission layer, wherein the protective layer has holes extending in an electron emission direction.

The holes advantageously have a diameter d between 10 µm and 100 µm.

The present invention additionally relates to a method for generating free electrons of defined low energy via an external photoelectric effect emitter, comprising the steps of: releasing electrons from the electron emission layer using the one or more UV LEDs, and accelerating the released electrons via an electric field generated by applying a voltage between the electron emission layer and the at least one electrode.

The present invention further relates to a method for collecting particles using a particle collection device, comprising the steps of: releasing electrons from the electron emission layer, using the one or more UV LEDs, accelerating the released electrons via an electric field generated by applying a voltage between the electron emission layer and the at least one electrode, electrically charging particles by the accelerated electrons, and accelerating the electrically charged particles by means of a second electric field by applying a voltage to the electrically chargeable plates.

The present invention additionally relates to a method for generating free electrons of defined low energy via a tunnel surface emitter, comprising the steps of releasing electrons from the electron emission layer by applying a voltage between the electron emission layer and the metal layer, and accelerating the released electrons via an electric field generated by applying a voltage between the electron emission layer and the at least one electrode.

The present invention further relates to a method for generating free electrons of defined low energy via a semiconductor based direct emitter, comprising the steps of: generating electrons in a boundary region between an n doped region and a p doped region, accelerating the electrons in the boundary region by an externally applied electric field, generating released electrons by tunnelling the electrons through an insulator layer that can be tunneled through and through an electron emission layer, and accelerating the released electrons via a second electric field generated by applying a voltage between the electron emission layer and the at least one electrode.

A direction of emission can, for example, be imposed on the released electrons, for example, by an internal electric field.

The present invention further provides a gas sensor comprising an external photoelectric effect emitter, an ion detection device, and a pressure reduction vessel in which the external photoelectric effect emitter and the ion detection device are arranged, wherein in operation of the gas sensor the pressure in the pressure reduction vessel is reduced relative to ambient pressure.

The invention also relates to a gas sensor comprising a tunnel surface emitter, or a semiconductor based direct emitter, an ion detection device, and a pressure reduction vessel in which the tunnel surface emitter or the semiconductor based direct emitter and the ion detection device are arranged, wherein in operation of the gas sensor the pressure in the pressure reduction vessel is reduced relative to the ambient pressure.

In an embodiment, the present invention relates to a gas sensor, wherein the pressure reduction vessel is sealed from uncontrolled gas ingress, has at least one gas inlet, and the at least one gas inlet comprises a gas permeable membrane.

The at least one gas permeable membrane can, for example, comprise polydimethylsiloxane (PDMS).

The at least one gas permeable membrane can, for example, have a thickness of 10 50 μm.

It can furthermore be provided that the pressure reduction vessel comprises a pumping device.

It can furthermore be provided that the pressure in the pressure reduction vessel during operation of the gas sensor is 100 to 200 mbar.

In an embodiment of the present invention, the ion detection device can, for example, comprise one or more Faraday cups.

The ion detection device may lastly comprise one or more secondary electron multipliers.

The present invention is based on the surprising finding that materials with low work functions can be produced by suitable metal alloys and electrons released from these can be accelerated to low energies with a narrow energy range by a suitable electron accelerating structure. Low energies in this context can, for example, be understood as energies in the range below 25 eV, for example, in the range below 10 eV. A low energy width can, for example, be understood to be an energy width of less than 1 eV, for example, of less than 0.5 eV, for example, of less than 0.1 eV.

Further features and advantages of the present invention can be found in the following description, in which an exemplary embodiment of the present invention is described with reference to the schematic drawings.

FIG. 1 shows a sectional view of an external photoelectric effect emitter 10 according to an embodiment of the present invention. The external photoelectric effect emitter 10 comprises an electron emitter structure 11, wherein the electron emitter structure 11 in turn comprises an atmosphere stable electron emission layer 17 of a mixture of metals having a first side and a second side, and an electron accelerating structure 18 on the first side of the electron emission layer 17. The electron emission layer 17 has a thickness between 1 nm and 10 nm.

The electron accelerating structure 18 comprises a plurality of electron accelerating elements 20. The electron accelerating structure 18 is suitable for accelerating charged particles, in particular electrons. The electron accelerating elements 20 are located above and are connected to the electron emission layer 17. The electron accelerating elements 20 in turn each have an electrode 22 and an electrically insulating structural element 24. The electrically insulating structural element 24 can, for example, be in direct contact above the electron emission layer 17. In operation, the electrodes 22 are positively or negatively charged relative to the electron emissions layer 17 via a voltage source (not shown). The electron accelerating structure 18 may optionally have cover electrodes (not shown) above the electrodes 22. By applying a zero potential or a repulsion potential, the region above the electrodes 22 can be set field free, which provides a free movement of the electrons 26 in an ionization space (not explicitly shown) adjacent to the electrodes 22.

The electron accelerating structure can also have a cylindrical control electrode (not shown). Such a cylindrical control electrode can be constructed in the form of a Wehnelt cylinder. With the cylindrical control electrode, the electrons can be focused on regions between the electron accelerating elements. This prevents, among other things, a charging of the electrically insulating structural elements 24.

The external photoelectric effect emitter 10 further comprises a substrate 12 made of a UV transparent material having a front side and a rear side. UV LEDs 14 are arranged adjacently the substrate 12 so that they emit light, shown as dashed arrows, in the direction of the transparent substrate 12. The UV LEDs 14 may alternatively be integrated into the substrate 12. The UV LEDs 14 can, for example, emit light of a wavelength between 240 nm and 400 nm. A reflective layer 16 is arranged on the rear of the substrate 12 and is suitable for reflecting the light emitted by the UV LEDs 14. For this purpose, the reflective layer 16 can, for example, comprises a material with a very high work function. A very high work function in this context means, for example, a work function of more than 4.5 eV, for example, of more than 5 eV. The material for this purpose can, for example, comprise platinum, mercury, nickel, palladium and iridium. The side of the substrate 12 facing away from the electron emission layer 17 can, for example, be structured so that the light emitted by the UV LEDs 14 can also be reflected several times in the direction of the electron emission layer 17. Surfaces that have an angle to the horizontal are, for example, suitable for this purpose. Due to the above mentioned multiple reflection, non-absorbed photons hit the electron emission layer 17 several times, increasing the absorption probability and enhancing the emission efficiency of the external photoelectric effect emitter.

In operation of the external photoelectric effect emitter 10, the UV LEDs 14 emit high energy photons in the UV range with wavelengths between approximately 240 nm to 400 nm. The photons strike the electron emission layer 17 either directly or after reflection from the reflective layer 16. The photons are absorbed by the electron emission layer 17 and release electrons 26 from it by the external photoelectric effect. Since the penetration depth of the photons is typically greater than the mean free path length of the electrons 26, grazing incidence of the light is advantageous to produce a sufficient number of free electrons 26. The grazing incidence is favored by the arrangement of the UV LEDs 14 to the side of the substrate. The electron accelerating structure 18 generates an electric field above the electron emission layer 17 via a voltage applied between the electrodes 22 and the electron emission layer 17, the electric field being substantially perpendicular to the surface of the electron emission layer 17 and accelerating the electrons 26. In the context of the electrons 26, the term acceleration is expressly intended to include positive and negative acceleration. Via the electron accelerating structure 18, the kinetic energy of the emitted electrons 26 can generally be adjusted by an accelerating voltage applied to the electrodes 22. The electron emission layer 17 is made of a material suitable for emitting electrons by the external photoelectric effect and has, for example, a low work function, for example, in the range between 2.5 to 3.6 eV. The length 1 of the acceleration path is of the same order of magnitude as or smaller than the mean free path length of the gas molecules. It can, for example, be 10 nm to 1 μm, for example, 30 nm to 300 nm.

The mixture of metals can, for example, comprise an alloy comprising two or more elements selected from As, Ag. Zn, Au, Pt, Ru, Rh, Pd, Os, Ir, Ce, Zn, Bi, Te, Sm, Eu, Gd, Yt, Yb, Nd, Pr and La. Alloys comprising InCe, AsCeSm, AgSm, AgCe, AgSmCe and AgAsCeSm are in particular suitable for forming the electron emission layer. The mixture of metals may alternatively comprise or consist of a eutectic. Suitable eutectics consist of at least one noble metal, at least one lanthanide, and at least one element selected from As, Te, Bi and Sn.

The mixture of metals can, for example, have a low work function of less than 3.5 eV. for example, less than 3.0 eV, and is produced by suitable alloys in accordance with the present invention. The exemplary compounds InCe, AsCeSm, AgSm, AgCe, AgSmeCe and AgAsCeSm exhibit constant work functions between 1.2 eV and 3.2 eV permanently (14 months of storage under normal conditions).

The generalized teaching on this class of materials is that the noble metals and the metals that occur "native" contribute to the alloy properties in that they increase the atmospheric stability of the alloy, while the lanthanides decrease the work function of the alloy. In addition, if the material is present in uniform stoichiometry, it can be deposited with greater crystalline order than if the material is present in non-uniform stoichiometry. This allows the noble metal atoms to better protect nearby lanthanide atoms from oxidation in air or reaction with atmospheric humidity. The increased stability can be explained by the so called spill-over effect. In the material groups mentioned here, electrons are transferred from the f orbitals of the noble metal atoms to the d orbitals of the lanthanide atoms. A uniform stoichiometry of the material AgCeSm is in particular advantageous for optimizing the low work function and the stability in respect of the atmosphere. The compounds $Ag_2(Ce_xSm_{1-x})$ and $Ag(Ce_xSm_{1-x})$ are particularly suitable for this purpose. These are, however, only examples of a large number of compounds based on these elements.

Alternatively or additionally, it is also possible to illuminate the electron emission layer 17 from the front side in order to release electrons therefrom. For this purpose, an electron accelerating structure 18 made of optically transparent materials is efficiency enhancing. The electrically insulating structural elements 24 may, for example, be made of quartz or a fluoride material for this purpose. The electrode can, for example, be made of transparent indium tin oxide (ITO). The UV LEDs are in this case arranged above the electron emission layer 17.

Figure 2:
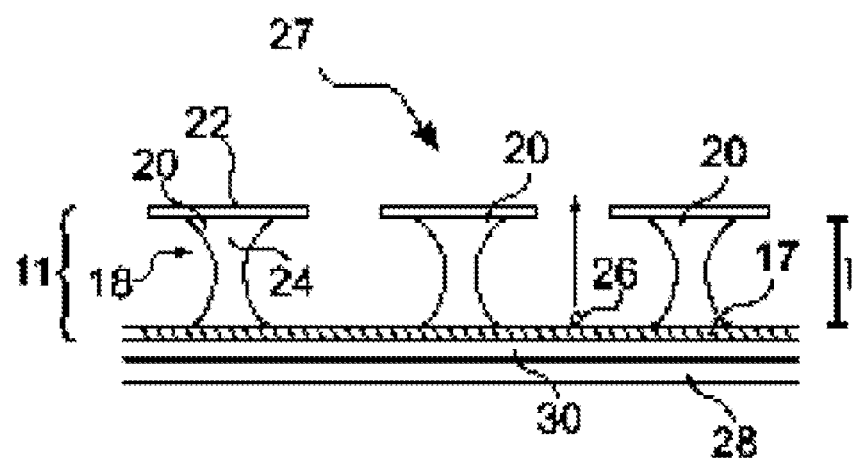
FIG. 2 shows a sectional view of a tunnel surface emitter according to an embodiment of the present invention.

FIG. 2 shows a sectional view of a tunnel surface emitter 27 according to a further embodiment of the present invention. The tunnel surface emitter 27 comprises an electron emitter structure 11, for example, according to the embodiment of the present invention shown in FIG. 1, an insulator layer 30 arranged on the second side of the electron emission layer 17, and a metal layer 28 arranged on the insulator layer 30 on a side facing away from the electron emission layer 17. The layer thicknesses of the metal layer 28, the insulator layer 30 that can be tunneled through, and the electron emission layer 17 that can be tunneled through, can, for example, each be between 0.5 nm and 6 nm, for example, between 1 nm and 3 nm. Both the metal layer 28 and the electron emission layer 17 are conductive. Strong electric fields can be generated within these layers by applying a voltage due to the thin insulator layer 30 between the two conductive layers. Electrons in the three layers mentioned can absorb energy from the electric field thus generated so that their average energy is above the equilibrium value corresponding to the lattice temperature. So called "hot electrons" generated in this way can emit from the anode 32 that can be tunneled through and from the electron emission layer 17 due to their high energy. Above the anode 32 that can be tunneled through, the tunnel surface emitter 27 comprises an electron accelerating structure 18 according to the embodiment of the present invention described in conjunction with FIG. 1. This electron accelerating structure 18 is capable of accelerating or decelerating the emitted electrons 26 in the same manner as the external photoelectric effect emitter 10 from FIG. 1.

Figure 3:
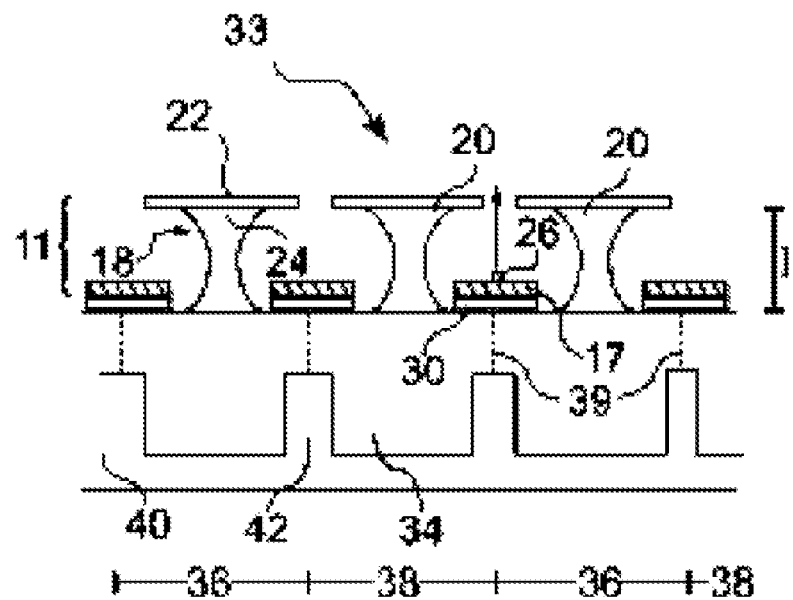
FIG. 3 shows a sectional view of a semiconductor based direct emitter according to an embodiment of the present invention.

FIG. 3 shows a cross section of a semiconductor based direct emitter 33 according to a further embodiment of the present invention. The semiconductor based direct emitter 33 comprises an electron emitter structure 11, for example, according to the embodiment of the present invention shown in FIG. 1, an insulator layer 30, which is arranged on the second side of the electron emission layer 17 and which has a layer thickness that can be tunneled through, and a semiconductor 34, which is arranged on a side of the insulator layer 30 facing away from the electron emission layer 17 and which has n doped regions 36 and p doped regions 38 horizontally next to one another. The semiconductor 34 has a direct large band gap of at least 3.0 eV. The semiconductor may, for example, comprise AlGaN or InAlGaN. There is a p n junction at each of the boundary regions 39, which are shown by vertical dashed lines, between the n and p doped regions 36, 38. The p n junctions are suitable for the emission of photons, by recombination of electrons and holes, for example, in a quantum film (not explicitly shown here), which has a lower band gap than the surrounding semiconductor material 34. The semiconductor material 34 thereby forms a light emitting diode at each of the p n junctions. The semiconductor material 34 is adjacent to an insulator 40 on an underside. The insulator 40 has fingers 42 projecting into the semiconductor material 34 at the locations of the p n junctions. The fingers 42 reduce the size of the p n junctions in the light emitting diode while keeping the size of the n and p doped regions 36, 38 approximately constant. The charge carrier density at the p n junctions can be increased by restricting the p n junctions in this way.

On a first side of the semiconductor material 34 there are elements consisting of an insulator layer 30 that can be tunneled through and an electron emission layer 17 in a similar or identical manner as shown in FIGS. 1 and 2. As also shown in FIGS. 1 and 2, the semiconductor based direct emitter 33 further comprises an electron accelerating structure 18 for accelerating electrons released from the electron emission layer 17.

Both the insulator layer 30 that can be tunneled through and the electron emission layer 17 can each have a layer thickness between 0.5 nm and 5 nm. The interrupted electron emission layer 17 shown here merely illustrates an embodiment of the present invention. An uninterrupted insulator layer 30 and electron emission layer 17 can also be used.

If one of the light emitting diodes is operated by applying a voltage, free electrons and holes are generated in the conduction band and the valence band of the semiconductor material, respectively. If a positive voltage is applied to the electron emission layer 17 located above the boundary region 39 of the operated light emitting diode, an electron 26 generated in the boundary region 39 of the light emitting diode is additionally accelerated towards the electron emission layer 17. If the electron 26 is generated in the boundary region 39 sufficiently close to the insulator layer 30 and accelerated towards it, there is a possibility that recombination may be prevented. The electron 26 can instead tunnel through both the insulator layer 30 and the electron emission layer 17 due to their small layer thicknesses. A current of free electrons can thereby be generated outside the light emitting diode.

The semiconductor based direct emitter 33, also as shown in FIGS. 1 and 2, may furthermore comprise an electron accelerating structure 18 for accelerating electrons 26 released from the electron emission layer 17. This is, however, in principle only optional for such a semiconductor based direct emitter 33. The electron accelerating structure 18 can in principle also be omitted depending on the field of application of the semiconductor based direct emitter 33.

For current limiting of the emitter to avoid breakdown, the electron emission layer 17 in this embodiment can, for example, comprise semi metals, for example, arsenic, selenium, antimony, tellurium and bismuth. For compounds made of these elements, the space charge zones helpful for acceleration extend deeper than the first atomic layer. A perovskite material, i.e., a material with a preferred axis of the k vector, can, alternatively be used for this purpose. The momentum distribution of the excited electrons is basically unidirectional In the emissive layer. A vertical preferred direction of the momentum distribution is generated through mechanical stress in the plane. A perovskite lattice structure is particularly suitable for this purpose.

Figure 4:
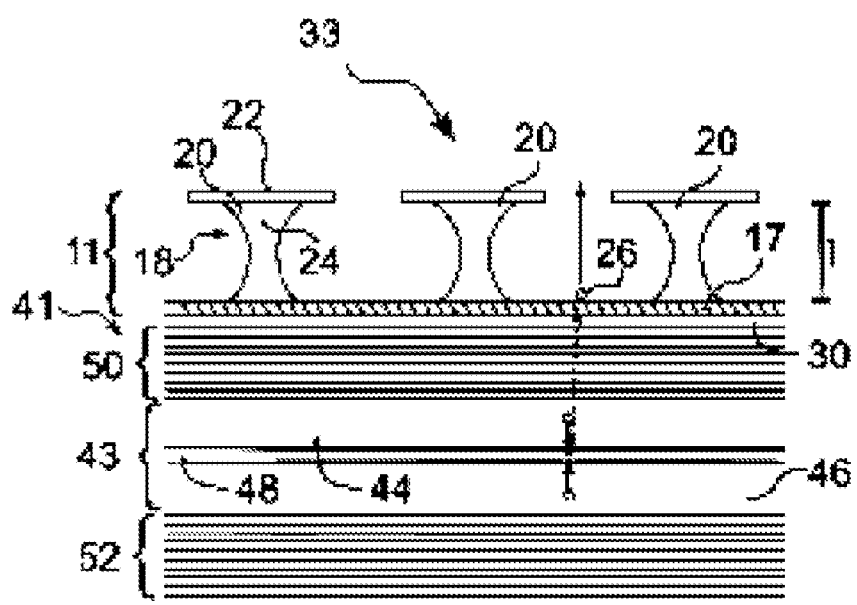
FIG. 4 shows a sectional view of a further semiconductor based direct emitter according to an embodiment of the present invention.

FIG. 4 shows a sectional view of another semiconductor based direct emitter 33 according to an embodiment of the present invention. This embodiment of the present invention has many of the elements described in conjunction with FIG. 2. The elements denoted by the same reference signs correspond to those shown in FIG. 2. The semiconductor based direct emitter 33 in particular also comprises an electron emitter structure 11, for example, according to the embodiment of the invention shown in FIG. 1, and an insulator layer 30. On a side of the insulator layer facing away from the electron emission layer 17, there is arranged a vertical cavity surface emitting laser (VCSEL) 41. The VCSEL 41 has a cavity 43, an upper Bragg mirror 50, and a lower Bragg mirror 52. The cavity 43 in turn has an n doped layer 44, a p doped layer 46, and a quantum film 48. The upper and lower Bragg mirrors 50, 52 are each in direct contact with the cavity 43. The band gap of the quantum film 48 is smaller than that of the surrounding n and p doped layers 44, 46.

During operation of the semiconductor based direct emitter 33, electrons from the n doped layer 44 recombine with holes from the p doped layer 46 in the quantum film 48 to produce photons of suitable wavelength, which are reflected multiple times by the upper and lower Bragg mirrors 50, 52 and release further photons from the quantum film 48 by stimulated emission. The upper Bragg mirror 50 has a lower reflectivity than the lower Bragg mirror 52. The VCSEL 41 thereby emits photons towards the electron emission layer 17. The photoelectric effect releases an electron 26 in the electron emission layer 17. The electron can then be accelerated or decelerated by the electron accelerating structure 18. The processes are shown schematically by the solid and dashed arrows. A side emitting semiconductor laser or even a light emitting diode can be used as an alternative to the VCSEL 41.

Figure 5:
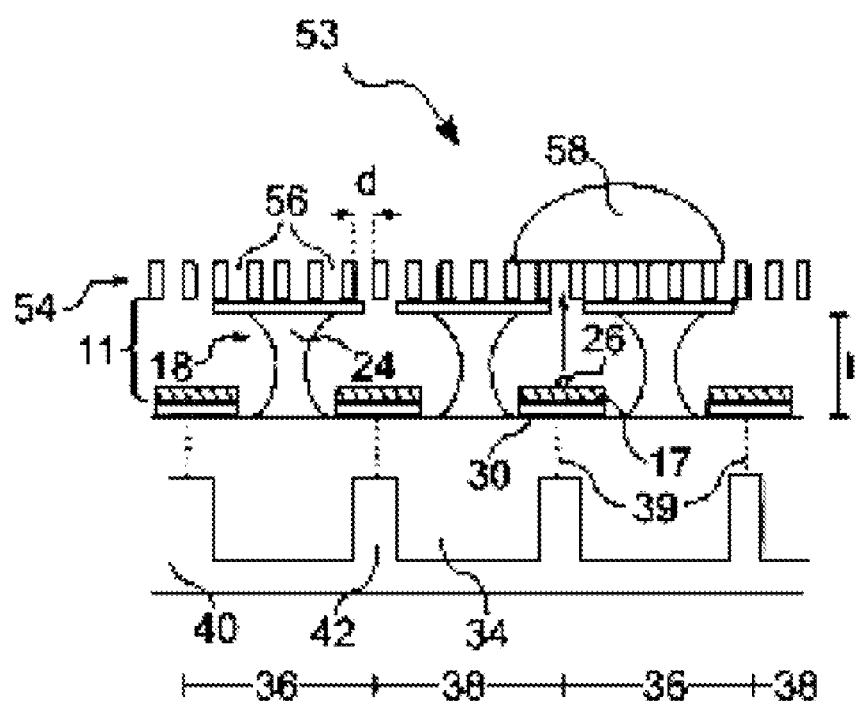
FIG. 5 shows a sectional view of a liquid ionizer according to an embodiment of the present invention.

FIG. 5 shows a sectional view of a liquid ionizer 53 according to an embodiment of the present invention. The liquid ionizer 53 is used for ionizing liquids or for delivering electrons 26 of a defined energy into liquids. The liquid ionizer 53 comprises a semiconductor based direct emitter 33, for example, according to the embodiment of the present invention shown in FIG. 3 therefor. However, any of the embodiments of the present invention according to FIG. 1, 2 or 4 may, for example, alternatively serve as the basis for the liquid ionizer 53. The liquid ionizer 53 comprises a protective layer 54 arranged on a side of the electron accelerating structure 18 facing away from the electron emission layer 17. The protective layer 54 allows the emission of electrons 26 through holes 56 located in the protective layer 54. The holes 56 have a diameter d selected so that a liquid 58 applied to the protective layer 54 does not penetrate through the holes due to its surface tension, and the electron emission is restricted as little as possible. The protective layer 54 additionally serves to protect the electrodes 22 and the electron emission layer 17 from reactions with the liquid 58. The protective layer can, for example, consist of an insulating polymer, such as fluorocarbon or fluorosilicone layers. The latter two materials enhance, among other things, the liquid repelling lotus blossom effect. The diameter d of the holes 56 can, for example, be between 10 µm and 100 µm, for example, between 20 µm and 50 µm. As described above, the electrons emit away from the electron emission layer 17, are accelerated or decelerated by the electron accelerating structure 18, fly through the holes 56 of the protective layer 54, and strike the surface of the liquid 58. The electron emission on liquid surfaces leads locally to strong changes in the surface energies. As a result, electrons are no longer diffusively provided with a broad energy spectrum, but with energies as they are exactly needed for a certain reaction process. This is helpful, for example, in catalysis or electrochemical reactions. This makes it possible to control reaction processes in a more targeted manner than was previously possible with catalysts or morphologies of reactive surfaces.

Figure 6:
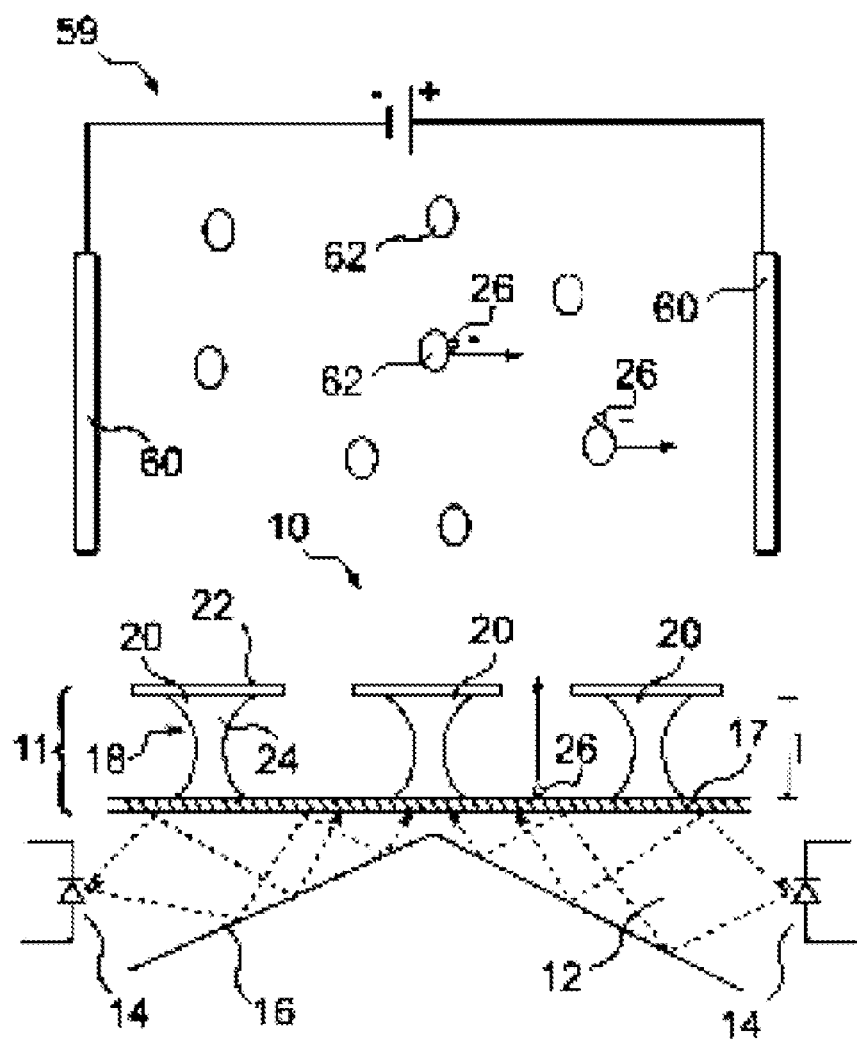
FIG. 6 shows a sectional view of a particle collection device according to an embodiment of the present invention.

FIG. 6 shows a particle collection device 59 according to an embodiment of the present invention and can be used, for example, as shown here, in air that contains particles 62. The particle collection device 59 comprises an external photoelectric effect emitter 10, for example, according to the embodiment of the present invention shown in FIG. 1. However, any of the embodiments of the present invention shown in FIG. 2, 3 or 4 may, for example, alternatively serve as the basis for the liquid ionizer 53. Two plates 60 charged with a different polarity are arranged on the first side of the electron emission layer 17 at a distance from each other with each being perpendicular to the electron emission layer 17. The plates 60 are suitable for generating an electric field perpendicular to the direction of emission of the electrons 26. Electrons 26 emitted by the external photoelectric effect emitter 10 can be captured by particles 62 located between the plates 60 during operation of the particle collection device 59. The particles 62 themselves thereby become negatively charged. In the electric field generated by the plates 60, the negatively charged particles 62 are accelerated towards the positively charged plate 60 and can be captured either by the plate 60 itself or by a filter (not shown) located in front of the plate 60. They are removed from the air in this way.

Figure 7:
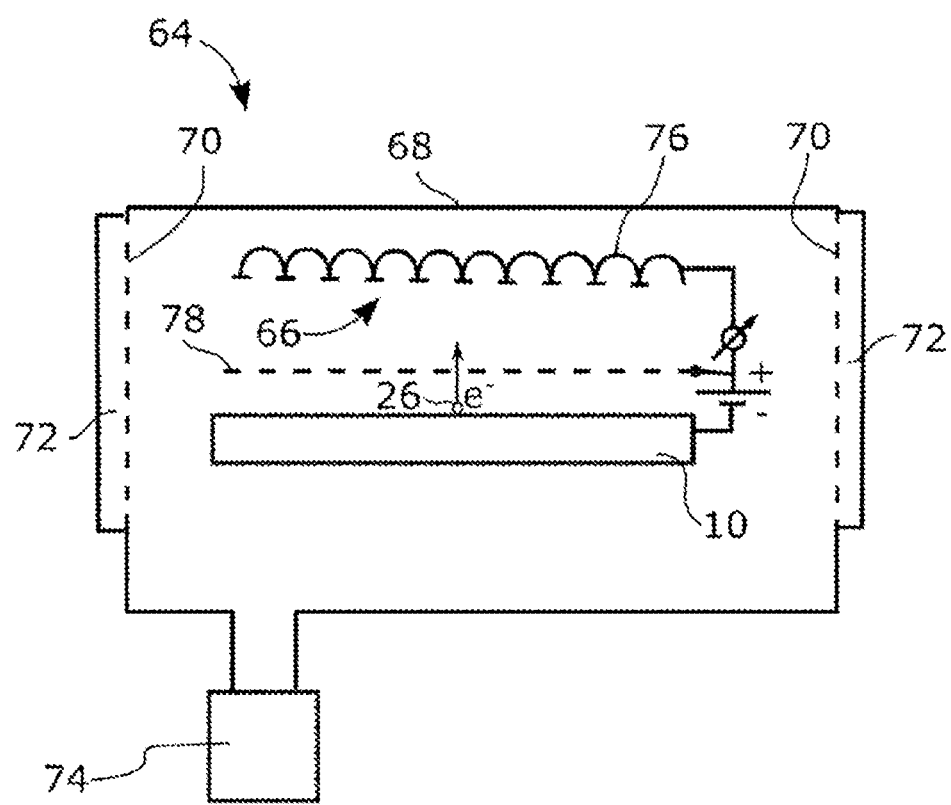
FIG. 7 shows a sectional view of a gas sensor according to an embodiment of the present invention.

FIG. 7 shows a sectional view of a gas sensor 64 according to an embodiment of the present invention. The gas sensor 64 is suitable for operation in a gas atmosphere and comprises an external photoelectric effect emitter 10, an ion detection device 66, and a pressure reduction vessel 68. The pressure reduction vessel 68 is sealed from uncontrolled gas ingress for this purpose. The external photoelectric effect emitter 10 and the ion detection device 66 are arranged within the pressure reduction vessel 68. The gas sensor 64 is configured to reduce the pressure inside the pressure reduction vessel 68 relative to a pressure outside the pressure reduction vessel 68. For this purpose, a pumping device 74 is arranged on the pressure reduction vessel 68 which pumps gas out of the pressure reduction vessel 68 during operation of the gas sensor. The pumping device 74 can, for example, be a diaphragm pump or another suitable pumping device 74 which is suitable for reducing the pressure inside the pressure reduction vessel 68.

The pressure reduction vessel 68 can, for example, have at least one gas inlet 70 for the controlled ingress of gas into the pressure reduction vessel 68. The pressure inside the pressure reduction vessel 68 can be controlled by the pumping capacity of the pumping device 74 and the size of the gas inlet 70. During operation of the gas sensor 64, the pressure inside the pressure reduction vessel 68 is basically reduced relative to the ambient pressure.

One or more valves (not shown here) for controlling the pressure can alternatively or additionally be fitted, for example, to the gas inlet 70 and/or to an inlet of the pumping device 74. In the embodiment of the present invention shown in FIG. 7, two gas inlets 70 are covered with a gas permeable membrane 72 each. The gas permeable membrane 72 can, for example, comprise a material that is at least partially permeable to trace gases, but which does not allow air moisture to pass through and/or is absorptive. This can, for example, improve the stability of the electron emission layer 17 of the external photoelectric effect emitter 10.

A suitable material for this purpose is, for example, polydimethylsiloxane (PDMS). The gas permeable membrane 72 may comprise PDMS or may consist of PDMS. The arrangement of the one or more gas inlets 70 and the pumping device 74 on the pressure reduction vessel 68 allows the direction of flow of the gas within the pressure reduction vessel 68 to be controlled.

The pressure in the pressure reduction vessel 68 during operation of the gas sensor can, for example, be between 50 500 mbar, for example, between 100 200 mbar. Due to the pressure reduction, the gas sensor 64 is passed through actively. A change in the gas composition outside the gas sensor 64 thus also affects the gas composition inside the gas sensor 64 within a short time.

During operation of the gas sensor 64, electrons 26 are emitted from the external photoelectric effect emitter 10. The emitted electrons 26 can be accelerated to a certain energy via an optional accelerating structure 78. The electrons 26 subsequently strike gas molecules which are ionized. The ionized gas molecules are detected by the ion detection device 66. The ion detection device 66 may comprise one or more Faraday cups 76 for this purpose. Alternatively or additionally to the Faraday cups, it may be provided that the ion detection device 66 comprises one or more secondary electron multipliers (not shown here).

Alternatively, or additionally to the external photoelectric effect emitter 10, it may be provided that the gas sensor 64, for the emission of electrons, comprises a tunnel surface emitter 27 and/or a semiconductor based direct emitter 33 according to one of the embodiments described in conjunction with FIGS. 3 and 4. The operating principle of the gas sensor 64 in these embodiments of the present invention is analogous to the operating principle described in conjunction with FIG. 7.

The features of the present invention disclosed in the foregoing description, in the drawings, as well as in the appended claims may be essential, both individually and in any combination, for the realization of the present invention in its various embodiments.

LIST OF REFERENCE SIGNS

10 external photoelectric effect emitter
11 electron emitter structure
12 substrate
14 UV LED
16 reflective layer
17 electron emission layer
18 electron accelerating structure
20 electron accelerating element
22 electrode
24 electrically insulating structural element
26 electron
27 tunnel surface emitter
28 metal layer
30 insulator layer
32 anode (that can be tunneled through)
33 semiconductor based direct emitter
34 semiconductor/semiconductor material
36 n doped region
38 p doped region
39 boundary region
40 insulator
41 vertical cavity surface emitting laser/VCSEL
42 finger
43 cavity
44 n doped layer
46 p doped layer
48 quantum film
50 upper Bragg mirror
52 lower Bragg mirror
53 liquid ionizer
54 protective layer
56 holes
58 liquid
59 particle collection device
60 plate
62 particle
64 gas sensor
66 ion detection device
68 pressure reduction vessel
70 gas inlet
72 gas permeable membrane
74 pumping device
76 Faraday cup
78 accelerating structure
l length of the acceleration distance
d diameter of the holes

What is claimed is:

1. An external photoelectric effect emitter comprising:
    an electron emitter structure comprising,
        an electron emission layer comprising a mixture of metals so as to be atmospherically stable, the electron emission layer being arranged to have a first side and a second side, and
        an electron accelerating structure arranged on the first side of the electron emission layer, the electron accelerating structure comprising at least one electrode which is electrically insulated from the electron accelerating structure so as to form an acceleration path which is configured to allow electrons which are released from the electron emission layer to be selectively accelerated upon generation of an adjustable electric field,
    wherein,
        the acceleration path has a length l of from 10 nm to 1 μm;
    at least one UV LED which is configured,
        to release electrons from the electron emission layer, and
        to emit electromagnetic radiation at least partially onto the electron emission layer; and
    a substrate which is arranged on the second side of the electron emission layer,
    wherein,
        the at least one UV LED is configured to the emit the electromagnetic radiation at least partially onto the second side of the electron emission layer and is arranged at least one of outside and inside the substrate, and the substrate is at least partially transparent in an emission wavelength range of the at least one UV LED.

2. The external photoelectric effect emitter as recited in claim 1, wherein the mixture of metals is an alloy, wherein the alloy is at least one of, a compound selected from InCe, AsCeSm, AgSm, AgCe, AgSmCe and AgAsCeSm, and two or more elements selected from As, Ag, Zn, Au, Pt, Ru, Rh, Pd, Os, Ir, Ce, Zn, Bi, Te, Sm, Eu, Gd, Yt, Yb, Nd, Pr and La.

3. The external photoelectric effect emitter as recited in claim 1, wherein the mixture of metals comprises an eutectic comprising at least one noble metal, at least one lanthanide, and at least one element selected from As, Te, Bi and Sn.

4. The external photoelectric effect emitter as recited in claim 1, wherein the electron accelerating structure further comprises at least one insulating structural element which, together with the at least one electrode, forms at least one electron accelerating element.

5. The external photoelectric effect emitter as recited in claim 1, further comprising:

a reflective layer arranged on a side of the substrate which faces away from the electron emission layer.

6. The external photoelectric effect emitter as recited in claim 5, wherein the reflective layer comprises a material selected from platinum, mercury, nickel, palladium and iridium.

7. A particle collection device comprising:

an external photoelectric effect emitter comprising,
an electron emitter structure comprising,
an electron emission layer comprising a mixture of metals so as to be atmospherically stable, the electron emission layer being arranged to have a first side and a second side, and
an electron accelerating structure arranged on the first side of the electron emission layer, the electron accelerating structure comprising at least one electrode which is electrically insulated from the electron accelerating structure so as to form an acceleration path which is configured to allow electrons which are released from the electron emission layer to be selectively accelerated upon generation of an adjustable electric field,
wherein,
the acceleration path has a length l of from 10 nm to 1 μm, and
at least one UV LED which is configured,
to release electrons from the electron emission layer, and
to emit electromagnetic radiation at least partially onto the electron emission layer; and
two plates which are electrically chargeable with a different polarity for generating an electric field, the two plates being arranged on the first side of and perpendicular to the electron emission layer and at a distance from each other.

8. A method for collecting particles using the particle collection device as recited in claim 7, the method comprising:

releasing electrons from the electron emission layer using the at least one UV LED;
accelerating the released electrons via an electric field which is generated by applying a voltage between the electron emission layer and the at least one electrode;
electrically charging particles via the accelerated released electrons; and
accelerating the electrically charged particles via a second electric field which is generated by applying a second voltage between the two plates.

9. A tunnel surface emitter comprising:

an electron emitter structure comprising,
an electron emission layer comprising a mixture of metals so as to be atmospherically stable, the electron emission layer being arranged to have a first side and a second side, and
an electron accelerating structure arranged on the first side of the electron emission layer, the electron accelerating structure comprising at least one electrode which is electrically insulated from the electron accelerating structure so as to form an acceleration path which is configured to allow electrons which are released from the electron emission layer to be selectively accelerated upon generation of an adjustable electric field,
wherein,
the acceleration path has a length l of from 10 nm to 1 μm;
an insulator layer arranged on the second side of the electron emission layer, the insulator layer having a layer thickness of between 0.5 nm and 6 nm; and
a metal layer arranged on the insulator layer on a side which faces away from the electron emission layer, the metal layer having a layer thickness of between 0.5 nm and 6 nm,
wherein,
both a layer thickness of the electron emission layer and the layer thickness of the insulator layer is configured to be tunneled through.

10. A method for generating free electrons of a defined low energy via the tunnel surface emitter as recited in claim 9, the method comprising:

releasing electrons from the electron emission layer by applying a voltage between the electron emission layer and the metal layer; and
accelerating the released electrons via an electric field which is generated by applying a voltage between the electron emission layer and the at least one electrode.

11. A gas sensor comprising:

the tunnel surface emitter as recited in claim 9;
an ion detection device; and
a pressure reduction vessel in which the tunnel surface emitter and the ion detection device are arranged,
wherein,
a pressure in the pressure reduction vessel is reduced relative to an ambient pressure during an operation of the gas sensor.

12. The gas sensor as recited in claim 11, wherein, the pressure reduction vessel is sealed against an uncontrolled gas ingress,
the pressure reduction vessel comprises at least one gas inlet, and
the at least one gas inlet comprises a gas permeable membrane.

13. A semiconductor based direct emitter for use in a surface chemistry, the semiconductor based direct emitter comprising:

an electron emitter structure comprising,
an electron emission layer comprising a mixture of metals so as to be atmospherically stable, the electron emission layer being arranged to have a first side and a second side, and an electron accelerating structure arranged on the first side of the electron emission layer, the electron accelerating structure comprising at least one electrode which is electrically insulated from the electron accelerating structure so as to form an acceleration path which is configured to allow electrons which are released from the electron emission layer to be selectively accelerated upon generation of an adjustable electric field, wherein, the acceleration path has a length l of from 10 nm to 1 μm;

an insulator layer arranged on the second side of the electron emission layer, the insulator layer and having a layer thickness that is configured to be tunneled through; and a semiconductor arranged on a side of the insulator layer which faces away from the electron emission layer, the semiconductor comprising n doped regions and p doped regions which are arranged to alternate one next to another, wherein, the n doped regions and the p doped regions have boundary regions which are adjacent to the insulator layer.

14. The semiconductor based direct emitter as recited in claim 13, further comprising:

an insulator arranged on a side of the semiconductor which faces away from the insulator layer, the insulator comprising fingers which are arranged at the boundary regions between the n doped regions and the p doped regions, the fingers being arranged to project into the semiconductor.

15. A method for generating free electrons of a defined low energy via the semiconductor based direct emitter as recited in claim 13, the method comprising:

generating electrons in the boundary regions between the n doped regions and the p doped regions;

accelerating the electrons in the boundary regions via an externally applied electric field;

generating released electrons by tunnelling the electrons through the insulator layer that is configured to be tunneled through and through the electron emission layer; and accelerating the released electrons via a second electric field which is generated by applying a voltage between the electron emission layer and the at least one electrode.

16. A gas sensor comprising:

the semiconductor based direct emitter as recited in claim 13;

an ion detection device; and a pressure reduction vessel in which the semiconductor based direct emitter and the ion detection device are arranged, wherein, a pressure in the pressure reduction vessel is reduced relative to an ambient pressure during an operation of the gas sensor.

17. A semiconductor based direct emitter comprising:

an electron emitter structure comprising, an electron emission layer comprising a mixture of metals so as to be atmospherically stable, the electron emission layer being arranged to have a first side and a second side, and an electron accelerating structure arranged on the first side of the electron emission layer, the electron accelerating structure comprising at least one electrode which is electrically insulated from the electron accelerating structure so as to form an acceleration path which is configured to allow electrons which are released from the electron emission layer to be selectively accelerated upon generation of an adjustable electric field, wherein, the acceleration path has a length l of from 10 nm to 1 μm;

an insulator layer arranged on a second side of the electron emission layer, the insulator layer having a layer thickness that is configured to be tunneled through; and a light emitting device selected from a VCSEL, a side emitting semiconductor laser or a light emitting diode, the light emitting device being arranged on a side of the insulator layer which faces away from the electron emission layer.

18. A method for generating free electrons of a defined low energy, the method comprising:

providing an external photoelectric effect emitter comprising, an electron emitter structure comprising, an electron emission layer comprising a mixture of metals so as to be atmospherically stable, the electron emission layer being arranged to have a first side and a second side, and an electron accelerating structure arranged on the first side of the electron emission layer, the electron accelerating structure comprising at least one electrode which is electrically insulated from the electron accelerating structure so as to form an acceleration path which is configured to allow electrons which are released from the electron emission layer to be selectively accelerated upon generation of an adjustable electric field, wherein, the acceleration path has a length l of from 10 nm to 1 μm, and at least one UV LED which is configured, to release electrons from the electron emission layer, and to emit electromagnetic radiation at least partially onto the electron emission layer;

releasing electrons from the electron emission layer using the at least one UV LED; and accelerating the released electrons via an electric field which is generated by applying a voltage between the electron emission layer and the at least one electrode.

19. A gas sensor comprising:

an external photoelectric effect emitter comprising, an electron emitter structure comprising, an electron emission layer comprising a mixture of metals so as to be atmospherically stable, the electron emission layer being arranged to have a first side and a second side, and an electron accelerating structure arranged on the first side of the electron emission layer, the electron accelerating structure comprising at least one electrode which is electrically insulated from the electron accelerating structure so as to form an acceleration path which is configured to allow electrons which are released from the electron emission layer to be selectively accelerated upon generation of an adjustable electric field, wherein, the acceleration path has a length l of from 10 nm to 1 µm, and at least one UV LED which is configured,
to release electrons from the electron emission layer, and
to emit electromagnetic radiation at least partially onto the electron emission layer;

an ion detection device; and a pressure reduction vessel in which the external photoelectric effect emitter and the ion detection device are arranged, wherein, a pressure in the pressure reduction vessel is reduced relative to an ambient pressure during an operation of the gas sensor.

20. The gas sensor as recited in claim 19, wherein, the pressure reduction vessel is sealed against an uncontrolled gas ingress, the pressure reduction vessel comprises at least one gas inlet, and the at least one gas inlet comprises a gas permeable membrane.

\* \* \* \* \*